(12) United States Patent
Benes

(10) Patent No.: US 8,106,361 B2
(45) Date of Patent: Jan. 31, 2012

(54) METHOD AND DEVICE FOR DETERMINING AN ALCOHOL CONTENT OF LIQUIDS

(75) Inventor: Roman Benes, Graz (AT)

(73) Assignee: Anton Paar GmbH, Graz-Strassgang (AT)

( * ) Notice: Subject to any disclaimer, the term of this patent is extended or adjusted under 35 U.S.C. 154(b) by 724 days.

(21) Appl. No.: 12/041,306

(22) Filed: Mar. 3, 2008

(65) Prior Publication Data
US 2008/0218733 A1    Sep. 11, 2008

(30) Foreign Application Priority Data

Mar. 1, 2007 (AT) .................................. A 330/2007

(51) Int. Cl.
*G01J 5/02* (2006.01)
(52) U.S. Cl. ................................................. 250/339.12
(58) Field of Classification Search .............. 250/343, 250/339.01–339.15, 340, 341.1–341.8, 342, 250/344, 345
See application file for complete search history.

(56) References Cited

U.S. PATENT DOCUMENTS

| | | | |
|---|---|---|---|
| 4,228,192 A * | 10/1980 | Sanden | 426/231 |
| 5,679,955 A | 10/1997 | Schmidt et al. | |
| 6,556,850 B1 * | 4/2003 | Braig et al. | 600/310 |
| 6,690,015 B1 | 2/2004 | Benes et al. | |
| 6,834,536 B2 | 12/2004 | Kempe | |
| 2002/0011567 A1 * | 1/2002 | Ozanich | 250/326 |
| 2006/0262309 A1 * | 11/2006 | Banks | 356/417 |
| 2009/0321646 A1 * | 12/2009 | Cozzolino | 250/339.05 |

FOREIGN PATENT DOCUMENTS

| | | |
|---|---|---|
| EP | 0760479 A2 | 3/1997 |
| JP | 06123700 A | 5/1994 |
| JP | 2001124695 A * | 5/2001 |

OTHER PUBLICATIONS

Austrian Search Report dated Jun. 28, 2007.

* cited by examiner

*Primary Examiner* — Kiho Kim
(74) *Attorney, Agent, or Firm* — Laurence A. Greenberg; Werner H. Stemer; Ralph E. Locher

(57) ABSTRACT

A method determines an alcohol content of liquids that contain at least water and alcohol as well as sugar or similar substances, in the liquid. The liquid is located in an analysis cell is irradiated by an IR-LED light source, which emits infrared radiation with $\lambda=1000$-$1500$ nm. The IR light absorption is measured at least two different wavelengths, and the measurement values are converted into data on the alcohol content of the liquid. The liquid is irradiated with a first IR radiation with a wavelength $\lambda 1$, where the absorption coefficient of the alcohol, and the absorption coefficient of the water, are identical in magnitude, and with at least a second IR radiation with a wavelength $\lambda 2$, where the absorption coefficients and are different. The absorption measurement values determined by an IR detector are applied to a calculating unit for the calculation of the alcohol content.

23 Claims, 4 Drawing Sheets

FIG.2    spectrum of a three-colored NIR-LED

METHOD AND DEVICE FOR DETERMINING AN ALCOHOL CONTENT OF LIQUIDS

CROSS-REFERENCE TO RELATED APPLICATION

This application claims the priority, under 35 U.S.C. §119, of Austrian application A 330/2007, filed Mar. 1, 2007; the prior application is herewith incorporated by reference in its entirety.

BACKGROUND OF THE INVENTION

Field of the Invention

The present invention relates to a novel method for the spectroscopic determination of the concentration of alcohols, particularly ethanol, and in liquid samples, particularly in alcohol-containing or ethanol-containing foods, drugs, cosmetic products, and similar products.

The spectroscopic determination of the concentration of alcohols, particularly ethanol, in liquid samples, is a widespread method where near infrared spectroscopy (NIR) is used for the qualitative and/or quantitative determination of a great variety of parameters.

The wavelength range in NIR spectroscopy extends here from approximately 700 to approximately 2500 nm; however, in this method one usually does not determine the fundamental oscillations, but the overtone and combination oscillations. However, in this wavelength range the absorption capacities of the substances to be examined are lower, the absorption bands broader, and they frequently overlap or are mutually superposed, which makes the interpretation of the measurement results difficult, and sometimes unequivocal measurements impossible.

The manufacture and availability of inexpensive components that can be used for spectroscopic examinations in this wave spectrum, for example, in the field of glass optics, semiconductor detectors and new light sources, have substantially enlarged the range of possibilities for a simple and rapid examination of samples by NIR spectroscopy using relatively simple installations to carry out the procedures.

A method of the type mentioned in the introduction for the spectroscopic determination of the concentration of lower alcohols, particularly ethanol, in liquid samples has been disclosed, for example, in U.S. Pat. No. 5,679,955, where the transmission measurements in the near infrared range are carried out, in each case at a single wavelength. Taking into account the fact that ethanol and water predominate by far in an alcohol-containing sample, the wavelength range used to carry out the measurements is chosen in this known method in such a way that the absorption of the water contained in the sample predominates compared to the absorption of the alcohol that is contained additionally in the sample.

Many calibration measurements, each at a given wavelength, are carried out, and then the alcohol content of additional samples is determined on the basis of the calibration data obtained, where, according to the known state of the art, it is proposed to carry out the measurements at wavelengths of approximately 0.98 µm, approximately 1.3 µm, and approximately 1.45 µm, taking into account the absorption coefficients of water and ethanol.

The disadvantage of this known method is thus the fact that the measurements are thus carried out at wavelengths at which the absorption coefficient of water predominates over that of ethanol, so that a determination of the alcohol content can only be carried out with a correspondingly low accuracy, and, furthermore, the determination of the alcohol content according to this U.S. Pat. No. 5,679,955 is limited to alcohol contents of less than 10 vol % alcohol.

Thus, this known method is substantially limited to the determination of the alcohol concentration of beers, whereas beverages, or in general liquid samples, with a higher alcohol content, such as, for example, wines, spirits, drugs, or also cosmetic products, cannot be examined with this known method. In addition, it is not possible to use this known method to take into account without problem third substances contained in the samples to be examined, which may in part have a considerable effect on the measurement result.

The hardware for this method is implemented preferably with one or more interference filter(s).

An additional method according to U.S. Pat. No. 6,690,015 B1 uses for the alcohol determination the absorption of IR light by the sample to be examined at least one wavelength in the range from 1100 nm to 1300 nm, preferably in the range from 1150 nm to 1250 nm. In this spectral range, alcohols present a very pronounced absorption maximum and thus they can be distinguished easily from the absorption spectrum of the water which constitutes the predominant proportion in such samples.

In a measurement of the absorption in this wavelength range, after a calibration which was carried out beforehand using either a synthetic or a real sample, for example, an ethanol-water mixture, beer, wine or a similar sample, the alcohol content of the sample to be examined can be determined directly.

However, besides alcohol and water, the content also includes third substances, which can influence the determination of the ethanol concentration in the sample to be examined. U.S. Pat. No. 6,690,015 B1 describes criteria to select working wavelengths from the wavelength range, where the absorption method presents, for additional substances contained in the sample presents, a substantially linear behavior, and this it is possible in a simple way to eliminate the influences caused by such additional substances in the measurement of the absorption and in the determination of the concentration. In this way, the alcohol determination is sufficiently precise and largely sample-independent in a concentration range up to 60% alcohol.

The method according to U.S. Pat. No. 6,690,015 B1 requires a high spectral resolution, and therefore a monochromator has to be used.

BRIEF SUMMARY OF THE INVENTION

It is accordingly an object of the invention to provide a method and a device for determining an alcohol content of liquids that overcomes the above-mentioned disadvantages of the prior art methods and devices of this general type. The purpose of the present invention now is to provide a spectroscopic method for determining an alcohol, particularly ethanol, content in liquid samples as mentioned above, by which the determination of the alcohol, particularly ethanol, content can be carried out over a broad concentration range in a simple and extremely cost effective way.

With the foregoing and other objects in view there is provided, in accordance with the invention, a method for determining a content of ethanol and of other monovalent alcohol in liquids, liquid samples containing at least water, ethanol or another alcohol, beverages, drugs, cosmetics, and for determining at least one additional content of extracts, sugars and fruit acid in the liquids. The method includes providing a liquid in an analysis cell or flowing the liquid through a throughflow cell, irradiating the liquid via at least one light source formed with an LED, the light source emitting infrared (IR) radiation with a wavelength in a range from 1000 to 1500 nm. More specifically by irradiating the liquid temporally successively or practically simultaneously with a first IR radiation with a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other and with at least a second IR radiation with a second wavelength $\lambda 2$, at which the absorption coefficient of the ethanol or the other monovalent alcohol, Epsalk$\lambda 2$, and the absorption coefficient of the water, Epsw$\lambda 2$, are different from each other. The IR light absorption is measured at least two different wavelengths of the infrared radiation resulting in measurement values and the measurement values are converted to data reflecting at least an alcohol content of the liquid. At least two real absorption values, which are determined currently by use of at least one IR detector, are forwarded to a calculating and display unit for calculating and displaying or printing out of at least the alcohol content of the liquid.

Thus, absorption of IR light at least two different wavelengths is used. These wavelengths are in the (±) vicinity around, or at, 1200 nm, where water and alcohol absorb at approximately the same level, and at 1300 nm and/or 1450 nm, where the two absorptions differ greatly.

An advantage of the invention relates in that—beyond the known use of infrared absorption in the NIR range for the characterization of the alcohol content—a measurement is carried out at different wavelengths with a detector which in itself is not specific, using inexpensive LEDs with a broad-band radiation characteristic, and without expensive monochromators.

As a result of the simultaneous simple temperature measurement and compensation of this influence by calculation, an additional expensive thermostatting component can also be omitted. This allows the production of a new category of devices, which are hand held, i.e., small and convenient, easy to operate and not difficult to transport, cost effective and inexpensive. They can be calibrated by anyone without great expense and without more detailed knowledge.

In comparison, a commercial alcohol content determination device with a grid spectrometer (such as, for example, the "Alcoholizer" from the company Paar) weighs at least approximately 10 kg and it has an incorporated monochromator, which is also disproportionately expensive.

It is important for the method according to the invention to use a linear relation between the alcohol concentration of the samples and the absorption of IR light by the sample at the given wavelength.

In accordance with an added mode of the invention, there is the step of irradiating the liquid to be examined with a third IR radiation with a third wavelength $\lambda 3$, at which the absorption coefficient of the ethanol or the other monovalent alcohol, Epsalk$\lambda 3$, is clearly different from the absorption coefficient of the water, Epsw$\lambda 3$ for increasing an accuracy of a result with regard to a content of the ethanol or the other monovalent alcohol and/or for compensation of turbidities in the liquid or for a determination of a content in the liquid of other components than ethanol or the other monovalent alcohol, the other components are sugar, extracts, dyes, fruit acids and/or dyes.

In accordance with an additional mode of the invention, there are the steps of irradiating the liquid to be examined with the first IR radiation with the first wavelength $\lambda 1$, at which the absorption coefficient of the ethanol and the other monovalent alcohol, Epsalk$\lambda 1$, and of the water, Epsw$\lambda 1$, which are substantially identical to each other, in each case are in a plus/minus vicinity of a maximum or at a maximum of a peak in the two wavelength-absorption coefficient diagrams or functions of the ethanol, the other monovalent alcohol and water; and irradiating the liquid to be examined with at least one of the second IR radiation and a third IR radiation with a wavelength $\lambda 2$ and $\lambda 3$, respectively, at which the absorption coefficients of the ethanol or the other monovalent alcohol, Epsalk$\lambda 2$ and/or Epsalk$\lambda 3$, and of the water, Epsw$\lambda 2$ and/or Epsw$\lambda 3$, are as different as possible from each other, and in each case are located in a plus/minus vicinity of a maximum or at a maximum of a peak in two wavelength-absorption coefficient diagrams or functions of the ethanol, the other monovalent alcohol and water.

In accordance with another mode of the invention, there is the step of using the infrared radiation from an IR radiation source which optionally emits simultaneously two or three different wavelengths $\lambda 1$, $\lambda 2$ and $\lambda 3$, where a peak maxima:
  a. of $\lambda 1$ are at 1160-1220 nm ($\lambda$=1200 nm, $\lambda 1200$);
  b. of $\lambda 2$ are at 1270-1320 nm ($\lambda$=1300 nm, $\lambda 1300$); and
  c. of $\lambda 3$ are at 1420-1470 nm ($\lambda$=1450 nm, $\lambda 1450$).

In accordance with a further mode of the invention, there is the step of using the IR radiation from an IR radiation source which optionally emits simultaneously two or three different wavelengths $\lambda 1$, $\lambda 2$ and $\lambda 3$, where a peak maxima:
  a. of $\lambda 1$ are at 1170-1190 nm ($\lambda$=1200 nm, $\lambda 1200$);
  b. of $\lambda 2$ are at 1290-1300 nm ($\lambda$=1300 nm, $\lambda 1300$); and
  c. of $\lambda 3$ are at 1425-1435 nm ($\lambda$=1450 nm, $\lambda 1450$).

In accordance with another added mode of the invention, there is the step of using the IR radiation from an IR radiation source which optionally emits simultaneously two or three different wavelengths $\lambda 1$, $\mu 2$ and $\lambda 3$, where a peak maxima:
  a. are at approximately 1180 nm ($\lambda$=1200 nm, $\lambda 1200$);
  b. at approximately 1295 nm ($\lambda$=1300 nm, $\lambda 1300$); and
  c. at approximately 1430 nm ($\lambda$=1450 nm, $\lambda 1450$).

In accordance with another further mode of the invention, there is the step of using broad-band IR radiation from an IR radiation source from a LED-IR light source, whose peaks present a width at half value in a range from 50 to 100 nm.

In accordance with an added mode of the invention, there is the step of using a photodetector associated with a LED-IR light source or integrated into the LED-IR light source, light intensity variations of the IR radiation are compensated or corrected.

In accordance with another added mode of the invention, there is the step of further measuring a density or an electrical conductivity of the liquid, and included in the evaluation together with results of corresponding comparison or calibration measurements.

In accordance with a further mode of the invention, for determining an alcohol concentration Calk in the liquid, there is the step of evaluating actual IR light absorption values A$\lambda 1$, A$\lambda 2$, A$\lambda 3$ which were obtained for the different wavelengths as well as additionally values of density and/or conductivity of the liquid by a linear approximation method chosen from the group of linear regression, multilinear regression and multiple regression, using appropriate reference values determined in previous calibration measurements.

In accordance with an additional mode of the invention, during the measuring step, keeping constant a temperature of a sample located in the analysis cell or flowing through the through flow cell, so that a determination of the IR light absorption of the liquid to be examined is carried out at constant temperature of the liquid and/or a currently measured temperature of the liquid to be examined is taken into consideration in an evaluation of the measurement results, or electronically compensated with software.

In accordance with another further mode of the invention, there is the step of keeping constant a temperature of the light source being an IR light source at least during an irradiation of the liquid and a determination of the value from its real absorption.

In accordance with yet another added mode of the invention, there are the steps of carrying out an IR absorption measurement with a device which contains the liquid to be examined and is disposed in the analysis cell or flows through the throughflow cell; providing at least one of a temperature sensor for determining a current liquid temperature and a device for thermostatting the liquid for keeping a sample temperature constant; and providing two facing windows, which are permeable to IR radiation, and the light source being an infrared-LED radiation source behind a first of the windows, the infrared-LED radiation source emitting one of simultaneously and sequentially, the IR radiation with one of at least two different wavelengths $\lambda 1$, $\lambda 2$, and with three different wavelengths $\lambda 1$, $\lambda 2$, $\lambda 3$, and an IR radiation detector behind a second of the windows, the IR radiation detector being connected with a calculating unit for processing the absorption measurement values determined by the IR radiation detector, and a display unit for one of displaying and printing out at least the content of ethanol or of the monovalent alcohol in the liquid.

In accordance with a concomitant mode of the invention, there is the step of carrying out the IR absorption measurement with a device, where a photodetector or another radiation intensity measuring unit is associated with, or integrated in or on, the infrared LED radiation source compensating or correcting variations in an intensity of the IR radiation emitted by the infrared LED radiation source, and connected with the calculating unit to allow data flow.

With the foregoing and other objects in view there is provided, in accordance with the invention, a device for determining a content of alcohol in liquids, and for determining at least one additional content of extracts, sugars and fruit acid in the liquids. The device contains a testing cell for receiving an aqueous liquid to be examined, the aqueous liquid containing ethanol or at least another alcohol, the testing cell is an analysis cell or a through flow cell through which the aqueous liquid flows. A temperature sensor is provided for determining a current temperature of the aqueous liquid. A device is provided for thermostatting the liquid for keeping a sample temperature constant. Two facing windows being permeable to IR radiation are provided. An infrared-LED radiation source is disposed behind a first one of the windows. The infrared-LED radiation source emits, simultaneously or sequentially, IR radiation with at least two different wavelengths $\lambda 1$, $\lambda 2$ or with three different wavelengths $\lambda 1$, $\lambda 2$, $\lambda 3$. An IR radiation detector is disposed behind a second one of the windows and is connected to a calculating unit for processing absorption measurement values determined by the detector. A display unit is provided for displaying or printing out at least a content of the ethanol or of the another alcohol in the liquid.

With the foregoing and other objects in view there is further provided, in accordance with the invention, a method for determining a content of ethanol and of another monovalent alcohol in liquids, liquid samples containing at least water and alcohol, beverages, drugs, cosmetics, and for determining at least one of additional content extracts, sugars and fruit acid in a liquid. The method includes providing the liquid in an analysis cell or flowing the liquid through a through flow cell, and irradiating the liquid via at least one light source formed with an LED, the light source emitting infrared radiation with a wavelength in the range from 1000 to 1500 nm. More specifically by irradiating the liquid temporally successively or practically simultaneously with a first IR radiation having a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other, and with a second IR radiation having a second wavelength $\lambda 2$, where the absorption coefficient of the ethanol or the other monovalent alcohol, Epsalk$\lambda 2$, is greater than the absorption coefficient of the water, Epsw$\lambda 2$. IR light absorption is measured at least two different wavelengths of the infrared radiation resulting in measurement values and the measurement values are converted to data of at least an alcohol content of the liquid. In each case at least two real absorption values are determined, via at least one IR detector. The two real absorption values are sent to a calculating and display unit for a calculation and displayed or printed out of at least the alcohol content of the liquid.

Other features which are considered as characteristic for the invention are set forth in the appended claims.

Although the invention is illustrated and described herein as embodied in a method for the determination of the alcohol content of liquids, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

According to the invention, IR radiation with third wavelengths that differ from the first mentioned different wavelengths is used, where, in the context of the present invention, "a wavelength" always refers to a relatively small wavelength range, for example, approximately ±50 nm around the precisely indicated wavelengths.

In accordance with an addition mode of the invention, information about the places in the absorption spectrum of NIR radiation that are advantageous for as precise as possible an analysis are provided.

In accordance with further modes of the invention, one can obtain the most advantageous NIR wavelength ranges and discrete wavelengths for the determination of the content of ethanol.

According to the invention, the NIR light emitted by the light source in no way needs to be sharply monochromatic, rather the corresponding wavelength peak can also present a broader band, i.e., particularly a width at half value of approximately 50-100 nm.

Semiconductor light emitting diodes, i.e., LEDs, for example, have such widths at half value. According to the present invention, it is preferred to use IR light sources with 2 or 3 LEDs, where each LED emits its own wavelength, and the 2 or 3 different wavelengths are emitted simultaneously, and where neither a small interference filter nor a monochromator is needed. Here, each one of the LEDs is modulated with a different frequency, and the light energy recorded by the detector is then again demodulated, so that the IR light of each LED, which passes through the sample and is weakened in it to different degrees, can be measured separately.

According to another method that can be used according to the invention, each one of the LEDs emits in a rapid temporal succession its own IR light with its individual wavelength, and the detector measures separately for each wavelength the intensity of the IR light that exits from the sample. Naturally, this measurement method as well requires no interference filter or monochromator.

Figure 2:
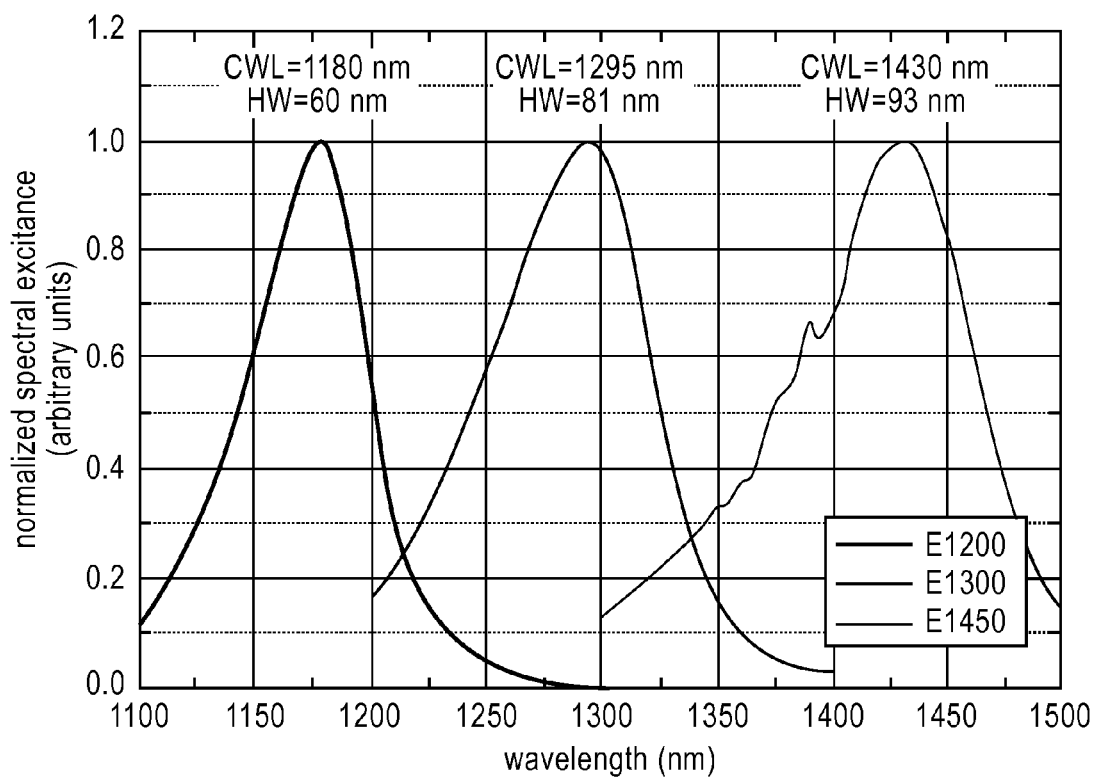
FIG. 2 is a graph showing a spectrum of a 3-color NIR-LED, i.e., a LED which is capable of emitting IR light at three different wavelengths.

The emission spectrum of such LEDs is shown in FIG. 2, where peak width at half value is approximately 70-90 nm.

In accordance with a further mode of the invention, a correction of the intensity variations of the IR measurement, which further improves the accuracy of the alcohol determination is provided.

In accordance with another mode of the invention, there is the step of providing measures that increase the accuracy of the measurement.

Accordingly another step of the invention provides information on an advantageous form of the evaluation of the measurement results of the IR detectors.

A further step of the invention teaches an exact determination of the temperature of the liquid to be examined is provided and/or this temperature is kept as exactly constant as possible.

Another feature of the invention shows that it is advantageous to keep the temperature of the IR light source constant, where, for example, the temperature can be maintained advantageously above room or environmental temperature by resistance heating.

Furthermore, a further feature of the invention relates to the novel alcohol content determination method, where an advantageous installation is used to carry out the method.

Furthermore, another feature of the invention relates to a new method, where an installation for compensating for variations in the intensity of the radiation put out by the IR radiation source or by its LEDs is used to increase the accuracy of the measurement.

Figure 3:
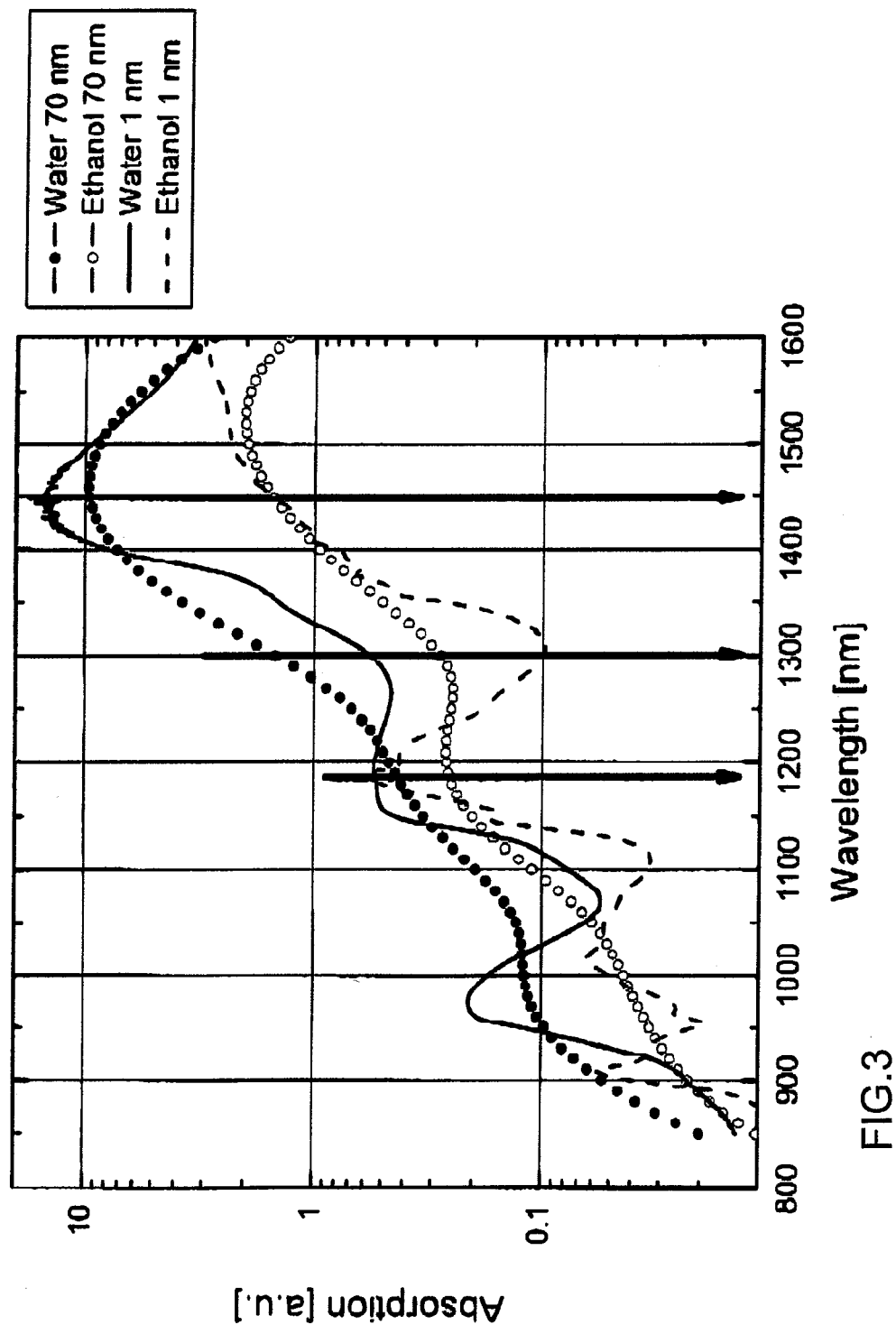
FIG. 3 is a graph showing an influence of a spectral resolution on an absorption spectra of water and ethanol.

Finally, the invention relates to a preferred device for carrying out the new alcohol determination method. The influence of the spectral resolution on the absorption spectra of water and ethanol can be seen very well from FIG. 3.

Although fine structures disappear from the spectrum if the spectral resolution is worse, the spectra nevertheless differ significantly from each other and, as has been found out, they can be used without greater problems for the determination of the concentration of alcohols, particularly ethanol.

Besides alcohol and water, real samples very often contain at least third substances, which can influence the determination of the ethanol concentration in the sample to be examined.

To be able to determine the actual alcohol content, the third substances must result in different contributions to the absorption at the measurement wavelengths.

Figure 4A:
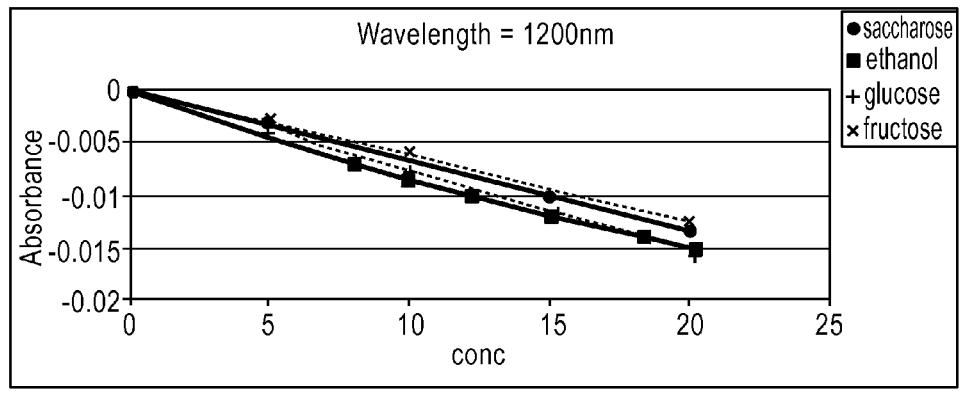
FIGS. 4A, 4B and 4C are graphs showing the relationship between the wavelength and absorption behavior.
Figure 4B:
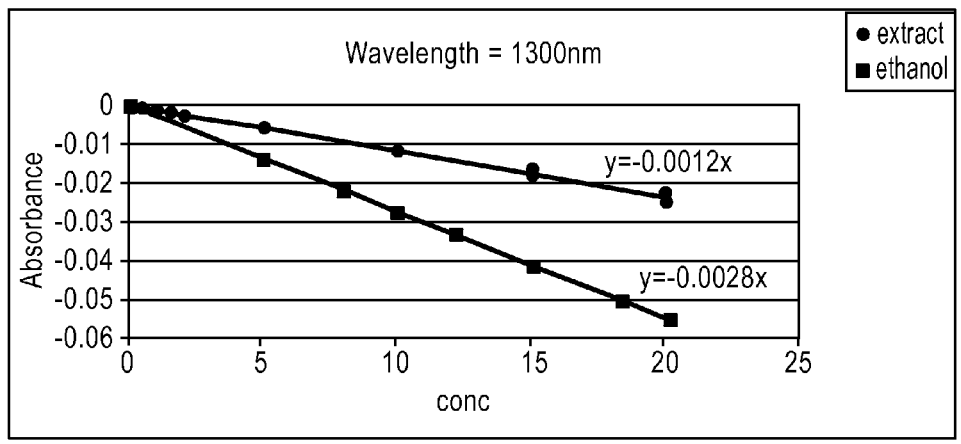
Figure 4C:
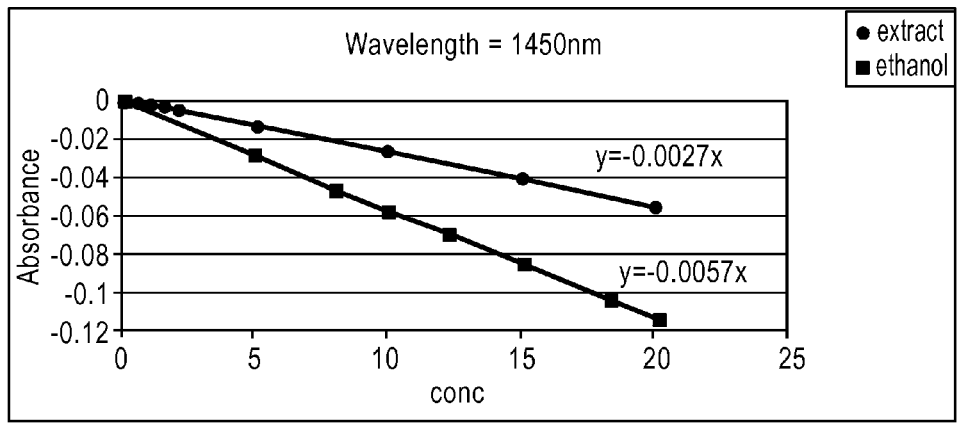

FIGS. 4A-4C show the absorption characteristic lines of alcohol and glucose, fructose and sucrose, which are essential extract components of beverages, at 1200 nm and at 1300 nm or 1450 nm, respectively. As can be seen in FIG. 4A, at a wavelength $\lambda=1200$ nm, all the components at in each case identical concentration absorb identically, but this is not the case at $\lambda=1300$ nm and at $\lambda=1450$ nm (FIGS. 4B, 4C). This difference in the absorption behavior makes the ethanol and the extract concentration measurement according to the invention possible.

The same also applies to organic acids, such as malic and tartaric acid, as well as to glycerol, which are often contained in beverages in addition to the sugar. The concentration characteristic lines at $\lambda=1300$ nm and $\lambda=1450$ nm are both linear and they present the same characteristic; therefore it does not matter in principle whether the wavelength $\lambda=1300$ nm or $\lambda=1450$ nm is used during the measurement. The only difference is in the "slope" of the characteristic lines of ethanol and extract, which at $\lambda=1450$ nm is approximately twice as much as at $\lambda=1300$ nm.

The accuracy of the determination of the alcohol concentration in an alcohol-containing sample is increased by the measurement of the absorption of IR light at three different wavelengths. The absorption measurement at approximately $\lambda=1300$ nm and $\lambda=1450$ nm provides substantially the same information; however, a turbidity correction can be used advantageously particularly with turbid samples.

Thus, by using IR light with at least two, particularly three, different wavelengths, the absorption values of the samples to be examined can be determined rapidly, allowing an evaluation of the measured value using simple evaluation methods, and then a simple comparison with previously determined reference values from at least one calibration measurement can be carried out.

For a simple evaluation of the values, which are determined, optionally simultaneously, at several wavelengths for the absorption of IR light by the sample to be examined, it is preferred, according to the invention, to evaluate, for the determination of the alcohol concentration, the absorption values obtained for IR light with different wavelengths by use of a linear approximation method, such as, for example, by linear regression, multilinear regression or similar methods, specifically taking into consideration reference values or constants that were obtained in the context of the calibration measurement(s), where, when such simple approximation methods are used, the result can be found to be satisfactory even without the aid of expensive evaluation and calculating methods.

To further increase the accuracy of the determination of the alcohol concentration in a liquid sample, the measurement of the absorption is also carried out at constant temperature of the samples to be examined and/or the current temperature of the sample to be examined is taken into consideration.

At constant temperature, or by thermostatting the liquid sample, the accuracy of the determination of the alcohol, particularly ethanol, concentration can be increased, or the temperature dependency of the individual parameters can also be taken into account by taking into account the actual sample temperature.

To achieve an appropriate accuracy in the determination of the ethanol concentration, which is advantageously better than 0.2 vol %, and, in particular, it is 0.1 vol %, it is moreover proposed to adjust the temperature of the sample preferably with an accuracy of 0.1° C., particularly <0.05° C., and to conduct the measurement at this temperature.

According to the invention, a NIR-LED is used as the light source. The NIR-LED is cost effective and its lifespan is almost unlimited, but it is extremely temperature sensitive. To achieve the necessary accuracy and stability of the measurement of the alcohol concentration, it is particularly advantageous to stabilize the temperature of the IR light source itself. This can be achieved, for example, by controlled electrical heating.

Figure 1:
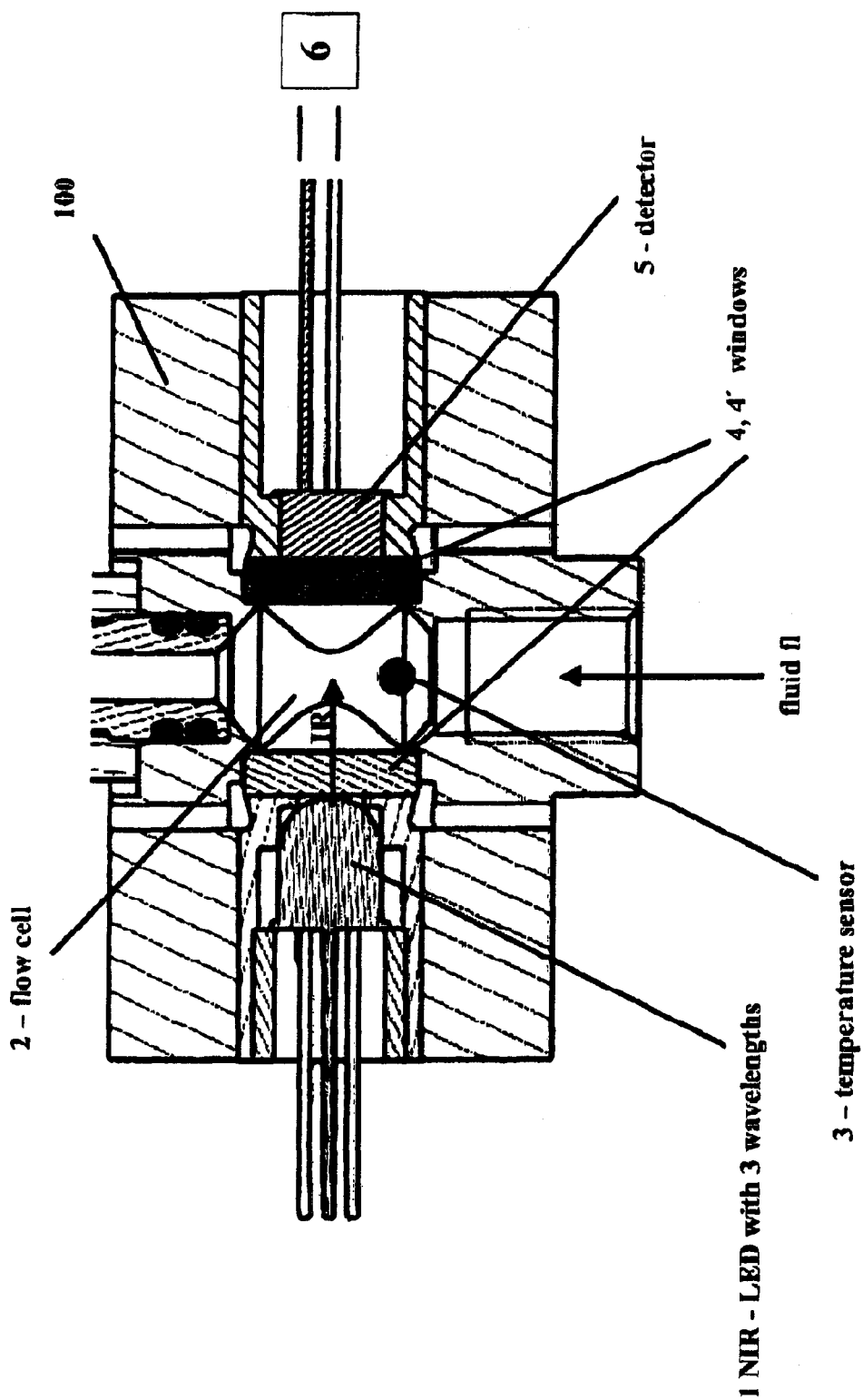
FIG. 1 is a diagrammatic, cross-sectional view of a device for determining a content of ethanol and of another monovalent alcohol in liquids, and for determining at least one additional content of extracts, sugars and fruit acid in the liquids according to the invention.

In a new device 100, which is represented in FIG. 1, and used in the context of the novel method for the spectroscopic determination of the concentration of alcohols in liquid samples, a liquid Fl flows through a throughflow cell 2 which receives the sample to be examined, where, as a light source 1, it is preferred to use a light emitting diode (LED) in the near infrared range (NIR), which is capable of emitting IR radiation at several wavelengths. Through a transparent window, for example, a special glass window 4, the electromagnetic IR radiation IR enters into the throughflow cell 1 which contains a liquid sample Pr to be examined, and then it reaches a detector 5 through an additional window 4'. Moreover, in the device shown, a sensor 3 is provided for the determination of the current temperature of the liquid Fl, and a sensor 3' for the control of the temperature of the LED 1.

The detector 5 differentiates between the wavelengths, i.e., at least 2 or even 3 absorption values can be measured simultaneously. For this purpose, the light emitting diodes are modulated electrically with different excitation frequencies. The signal from the detector 5 is again demodulated according to these three frequencies, and in this way three signals can be received practically simultaneously, which can each be assigned to one of the infrared wavelengths and then applied separately to the evaluation unit 6.

Naturally, it is also possible for the wavelength differentiation to be carried out in the time domain, i.e., a measurement is carried out with only one of three light emitting diodes within a certain time interval, and then with a second LED, and finally with a third LED.

FIG. 2 shows the spectrum of the 3-color NIR-LED, i.e., a LED which is capable of emitting IR light at three different wavelengths $\lambda 1$, $\lambda 2$ and $\lambda 3$. This NIR-LED, which is used preferably, possesses an integrated photodetector, which measures any variations in the light power of the LED and thus allows an on line correction of the absorption values of the samples.

If, for example, the absorption is measured at only one wavelength, one could not distinguish between alcohol and extract. In the case of a measurement at two or more different wavelengths, this becomes possible:

The absorption A, as already briefly indicated above, is substantially proportional to the concentration:

$$A = c1 \cdot Eps1 + c2 \cdot Esp2 + \ldots + cn \cdot Epsn,\qquad\text{a.}$$

wherein $c1, c2, \ldots cn$ denote the concentration of the given substances 1, 2, ... n and $Eps1, Eps2, \ldots Epsn$ denote the corresponding absorption coefficients of the substances.

If the substance constants or absorption coefficients of all the components in the sample, except those of alcohol, are approximately identical, and this is the case, the sample can be treated as if it were a system with only two components, formed of extract and alcohol.

The following then applies:

$$A1200 = Calk \cdot Epsalk1200 + Cext \cdot Epsext1200 \qquad\text{a.}$$

$$A1300 = Calk \cdot Epsalk1300 + Cext \cdot Epsext1300 \qquad\text{b.}$$

wherein A1200 and A1300 denote the total absorption at $\lambda=1200$ nm and $\lambda=1300$ nm; Epsalk1200 and Epsalk1300 denote the absorption or extinction coefficients of the alcohol at $\lambda=1200$ and $\lambda=1300$ nm; Epsext1200 and Epsext1300 denote the absorption coefficients of the extract in the liquid sample at $\lambda=1200$ and $\lambda=1300$ nm; Cext denotes the concentration of the extract in the liquid; and Calk denotes the concentration of the alcohol in the liquid sample.

The substance constants Epsext1200 and Epsext1300 are determined from previous measurements on corresponding binary solutions and thus known. They are the slopes of lines, as shown in FIGS. 4A-4C.

The following then holds for the alcohol concentration Calk of a sample, with a measurement at two different wavelengths $\lambda=1200$ and $\lambda=1300$:

$$Calk = A + B \cdot A1200 + C' \cdot A1300 \qquad\text{a.}$$

The absorption values A1200 and A1300 obtained at $\lambda=1200$ and $\lambda=1300$ nm are measurement values which the sensor or sensors 5 delivers or deliver. Then, from the two above equations with two unknowns, the two concentration values Calk and Cext of alcohol and extract are calculated.

In the real case, the light scattering is first compensated by a measurement at a third wavelength, particularly in the vicinity of $\lambda=1450$ nm, and only then the calculation and the evaluation are carried out, as indicated above.

Analogously, the following would hold in the case of an absorption determination using IR light with three chosen wavelengths by use of multilinear or multiple regression:

$$Calk = A + B \cdot A_{1200} + C' \cdot A_{1300} + D \cdot A_{1450} + E \cdot x \qquad\text{a.}$$

b. $E \cdot x$: Besides the absorptions (A), other components can also be included in the model, such as, particularly, the density or color value.

Thus, in the calibration test, measurements of n samples are carried out in each case, and the determined values for the constants A, B, C', D, E are determined for the concentrations determined on the basis of the results of reference methods. The described model is then used for the determination of the concentration of or in unknown samples.

The system of equations is to be solved in the usual way using the mathematical methods that are usually used for multiple regression.

The above-discussed binary ansatz with only two wavelengths according to two general equations $$A1200 = Calk \cdot Epsalk1200 + Cext \cdot Epsext1200 \qquad\text{a.}$$

$$A1300 = Calk \cdot Epsalk1300 + Cext \cdot Epsext1300 \qquad\text{b.}$$

has already been explained above. With the same binary ansatz, the measurement results are slightly less precise.

It is noted here that extensive literature exists on the method of multiple regression and multivariable analysis, respectively, which does not need to be discussed in greater detail here.

The invention is explained further in the following now described example.

Example: In an actual test series with a prototype of the novel absorption measurement apparatus to be used according to the method, the described simple structure was enlarged by the possibility of thermostatting the sample.

A throughflow cuvette with a 7-mm long optical path was incorporated in a metal block, whose temperature could be maintained between 10 and 40° C., and which functions simultaneously as a holder for the optical components.

On one side of the cuvette, a NIR-LED was mounted, and on the opposite side a Ge detector (EG&G, diameter 3 mm) was mounted as the signal detector.

As the NIR-LEDs, three infrared LEDs in a housing were used and operated with a modulated power supply.

For the compensation of the temperature influence of the LED, the LEDs were heated by a simple resistance wire winding around their cap. The temperature maintenance block in the embodiment as described above and in FIG. 1 is not provided, because here it is assumed that a particularly cost effective and convenient embodiment is used, and that appropriate temperature measurements by standard solutions and calibration, respectively, yield sufficiently accurate results.

Here, the current flow was chosen so that signals that could be detected well were obtained both at the IR detector, for example, Ge detector, and also at the reference detector. The modulation was carried out with frequencies of 170, 180 and 190 Hz.

The light technology equipment used the Epitex multi-wavelength LED L1200/1300/1450/PD-35B32 arrangement with indicated reference detector.

The detected photocurrents were translated into demodulated current values (trans-impedance amplifier and synchronously demodulating lock-in) and the collected data were further processed electronically (with PC card and LabView software). A large number of real samples was measured, on the one hand with reference laboratory apparatuses of the Alcolyzer Plus type with ±0.1% vol/vol accuracy) and also with the test structure—as described here—of the absorption measuring device according to the invention.

The measurement was carried out by the alternating measurement of water and sample, and correction or compensation with the water reference (Calk=0, Cext=0).

The extract of a sample can be calculated using the known Tabarié formula from the ethanol concentration and the density.

As examples, we present here, in tabular form, the basic results of seven of a total of 24 Austrian and foreign wine samples, which were examined to determine their alcohol content; the columns list, successively, the sample No., the wine examined with indication of its origin, the ethanol content determined with the commercial, complicated and expensive apparatus, the content of extract, and finally the percent contents of ethanol in the examined samples, as determined according to the invention, simply and inexpensively only on the basis of absorption measurements and on the basis of absorption measurements taking into account the density of the samples.

Thus, a total of 24 wine types (with 9-13.3 vol % alcohol) and 28 beer types (with 0-9.6 vol % alcohol) and a great variety of extract values were measured with a prototype of the new handheld apparatus (at $\lambda$=1180 nm ("$\lambda$ 1200"), $\lambda$=1295 nm ("$\lambda$1300"]) and $\lambda$=1430 nm ("$\lambda$ 1450"), and at the same time the following parameters were characterized for the examined samples with reference methods.

Alcohol content: The known Alcolyzer uses the specific absorption peak at 1180 nm for the concentration determination; the measurement was carried out in a thermostatted cuvette, and the wavelength adjustment with a grid spectrometer.

Density measurement with a DMA4500 throughflow density measuring apparatus of the company Paar, Austria (correlated linearly with the extract value of the sample).

Color measurement (for the beer samples).

In the test, measurements of n−1 samples were carried out in each case, and the determined values were used for the constants A, B, C', D, E for the concentration determination of the nth sample. Then a comparison was made to determine the agreement between the concentration value of the nth sample and the actual value from the reference determination.

The measurements for a total of 24 wine samples and 28 beer types were evaluated statistically; the following values of the standard error of cross validation (SECV) were obtained for the examined sample selections.

The SECV is calculated in the statistical evaluation of the models from the sum of the squares of the deviations from the actual reference value.

For the measured wine samples with the absorbances A1200, A1300, A1450 at $\lambda1$=approximately 1200 nm, $\lambda2$=approximately 1300 nm, $\lambda3$=approximately 1450 nm, and possibly additional parameters x in the regression model, the following results were obtained:

| Samples | Model parameters, values measured respectively taken into account | SECV (% vol/vol) |
|---|---|---|
| Wine | Absorption | 0.28 |
| Wine | Absorption and conductivity | 0.16 |
| Wine | Absorption and density | 0.09 |
| Beer | Absorption, density, and color | 0.06 |

TABLE 1

List of the wine samples

| No. | Sample, origin | Ethanol content, determined with the alcolyzer (% vol/vol) | Extract (% weight/volume) | Ethanol, *) determined with absorption % vol/vol | % Ethanol, **) determined with abs. + density % vol/vol |
|---|---|---|---|---|---|
| 2 | Merlot, France | 12.37 | 2.80 | 12.36 | 12.47 |
| 4 | Welschriesling Trunk 2003 | 12.43 | 1.65 | 12.29 | 12.38 |
| 5 | Galser Spätlese Cuvée Austria | 10.73 | 8.03 | 10.82 | 10.71 |
| 11 | Vino Tinto, Spain | 10.57 | 6.84 | 10.51 | 10.55 |
| 12 | Blauer Zweigelt 2003, Austria | 12.92 | 3.15 | 12.87 | 12.78 |
| 14 | Portugieser Weissherbst 2002, Austria | 8.80 | 5.92 | 9.03 | 8.84 |
| 21 | Ruby Cabernet | 12.87 | 3.52 | 13.28 | 12.88 | a. *) measured at 3 different wavelengths
b. **) measured at 3 different wavelengths For the first time the combination of two absorption values at different IR wavelengths is proposed here in spectra which themselves are broadly "smeared"—here originating from LED-IR sources. The two first IR wavelengths are at λ=approximately 1200 and λ=approximately 1300 nm; these are two wavelength vicinities by which the separation between alcohol and extract becomes possible.

In the case of the combination of the determination at the two IR wavelengths that have just been mentioned with the absorption measurement at a third IR wavelength λ=approximately 1450 nm, scattered light portions are taken into account additionally, and in this way the accuracy and the exactness of the measurement is increased.

The invention claimed is:

1. A method for determining a content of ethanol and of other monovalent alcohol in liquids, which comprises the steps of:
    obtaining a liquid including at least water, ethanol or another alcohol, and at least one additional substance selected from the group consisting of sugars and fruit acids;
    performing one of providing a liquid in an analysis cell and flowing the liquid through a throughflow cell;
    irradiating the liquid via at least one light source formed with an LED, the light source emitting infrared (IR) radiation with a wavelength in a range from 1000 to 1500 nm by the further step of:
    irradiating the liquid one of temporally successively and practically simultaneously with a first IR radiation with a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other and with at least a second IR radiation with a second wavelength $\lambda 2$, at which the absorption coefficient of the ethanol or the other monovalent alcohol, Epsalk$\lambda 2$, and the absorption coefficient of the water, Epsw$\lambda 2$, are different from each other;
    measuring IR light absorption at least two different wavelengths of the infrared radiation resulting in measurement values;
    converting the measurement values to data reflecting at least an alcohol content of the liquid;
    forwarding in each case at least two real absorption values, which are determined currently by use of at least one IR detector, to a calculating and display unit for one of calculating and displaying and printing out of at least the alcohol content of the liquid;
    irradiating the liquid to be examined with a third IR radiation with a third wavelength $\lambda 3$, at which the absorption coefficient of the ethanol or the other monovalent alcohol, Epsalk$\lambda 3$, is clearly different from the absorption coefficient of the water, Epsw$\lambda 3$;
    performing the step of irradiating the liquid to be examined with the third IR radiation for increasing an accuracy of a result with regard to at least one of a content of the ethanol or the other monovalent alcohol and for at least one of compensation of turbidities in the liquid and for a determination of a content in the liquid of other components than ethanol or the other monovalent alcohol, the other components being selected from the group consisting of sugar, extracts, dyes, fruit acids and dyes;
    using the infrared radiation from an IR radiation source which optionally emits simultaneously two or three different wavelengths $\lambda 1$, $\lambda 2$ and $\lambda 3$; and
    using broad-band IR radiation from an IR radiation source from a LED-IR light source, whose peaks present a width at half value in a range from 50 to 100 nm.

2. The method according to claim 1, wherein a peak maxima:
    of $\lambda 1$ is at 1160-1220 nm,
    of $\lambda 2$ is at 1270-1320 nm, and
    of $\lambda 3$ is at 1420-1470 nm.

3. The method according to claim 1, which further comprises:
    irradiating the liquid to be examined with the first IR radiation with the first wavelength $\lambda 1$, at which the absorption coefficient of the ethanol and the other monovalent alcohol, Epsalk$\lambda 1$, and of the water, Epsw$\lambda 1$, which are substantially identical to each other or at a maximum of a peak in the two wavelength-absorption coefficient diagrams or functions of the ethanol, the other monovalent alcohol and water; and
    irradiating the liquid to be examined with at least one of the second IR radiation and a third IR radiation with a wavelength $\lambda 2$ and $\lambda 3$, respectively, at which the absorption coefficients of the ethanol or the other monovalent alcohol, Epsalk$\lambda 2$ and/or Epsalk$\lambda 3$, and of the water, Epsw$\lambda 2$ and/or Epsw$\lambda 3$, are as different as possible from each other, and in each case are located in a plus/minus vicinity of a maximum or at a maximum of a peak in two wavelength-absorption coefficient diagrams or functions of the ethanol, the other monovalent alcohol and water.

4. The method according to claim 3, which further comprises using the IR radiation from an IR radiation source which optionally emits simultaneously two or three different wavelengths $\lambda 1$, $\lambda 2$ and $\lambda 3$, where a peak maxima:
    of $\lambda 1$ is at 1170-1190 nm;
    of $\lambda 2$ is at 1290-1300 nm; and
    of $\lambda 3$ is at 1425-1435 nm.

5. The method according to claim 3, which further comprises using the IR radiation from an IR radiation source which optionally emits simultaneously two or three different wavelengths $\lambda 1$, $\lambda 2$ and $\lambda 3$, where a peak maxima:
    of $\lambda 1$ is at approximately 1180 nm;
    of $\lambda 2$ is at approximately 1295 nm; and
    of $\lambda 3$ is at approximately 1430 nm.

6. The method according to claim 1, which further comprises during the measuring step, keeping constant a temperature of a sample located in the analysis cell or flowing through the through flow cell, so that a determination of the IR light absorption of the liquid to be examined is carried out at constant temperature of the liquid and/or a currently measured temperature of the liquid to be examined is taken into consideration in an evaluation of the measurement results, or electronically compensated with software.

7. The method according to claim 1, which further comprises keeping constant a temperature of the light source being an IR light source at least during an irradiation of the liquid and a determination of the value from its real absorption.

8. The method according to claim 1, which further comprises:
    carrying out an IR absorption measurement with a device which contains the liquid to be examined and is disposed in the analysis cell or flows through the throughflow cell;
    providing at least one of a temperature sensor for determining a current liquid temperature and a device for thermostatting the liquid for keeping a sample temperature constant; and providing two facing windows, which are permeable to IR radiation, and the light source being an infrared-LED radiation source behind a first of the windows, the infrared-LED radiation source emitting one of simultaneously and sequentially, the IR radiation with one of at least two different wavelengths $\lambda 1$, $\lambda 2$, and with three different wavelengths $\lambda 1$, $\lambda 2$, $\lambda 3$, and an IR radiation detector behind a second of the windows, the IR radiation detector being connected with a calculating unit for processing the absorption measurement values determined by the IR radiation detector, and a display unit for one of displaying and printing out at least the content of ethanol or of the monovalent alcohol in the liquid.

9. The method according to claim 8, which further comprises carrying out the IR absorption measurement with a device, where a photodetector or another radiation intensity measuring unit is associated with, or integrated in or on, the infrared LED radiation source for one of compensating and correcting variations in an intensity of the IR radiation emitted by the infrared LED radiation source, and connected with the calculating unit to allow data flow.

10. A method for determining a content of ethanol and of other monovalent alcohol in liquids, liquid samples containing at least water, ethanol or another alcohol, beverages, drugs, cosmetics, and for determining at least one additional content of extracts, sugars and fruit acid in the liquids, which comprises the steps of:
   performing one of providing a liquid in an analysis cell and flowing the liquid through a throughflow cell;
   irradiating the liquid via at least one light source formed with an LED, the light source emitting infrared (IR) radiation with a wavelength in a range from 1000 to 1500 nm by the further step of:
      irradiating the liquid one of temporally successively and practically simultaneously with a first IR radiation with a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other and with at least a second IR radiation with a second wavelength $\lambda 2$, at which the absorption coefficient of the ethanol or the other monovalent alcohol, Epsalk$\lambda 2$, and the absorption coefficient of the water, Epsw$\lambda 2$, are different from each other;
   measuring IR light absorption at least two different wavelengths of the infrared radiation resulting in measurement values;
   converting the measurement values to data reflecting at least an alcohol content of the liquid;
   forwarding in each case at least two real absorption values, which are determined currently by use of at least one IR detector, to a calculating and display unit for one of calculating and displaying and printing out of at least the alcohol content of the liquid; and
   using a photodetector to compensate or correct light intensity variations of the IR radiation;
   wherein the photodetector is associated with a LED IR light source or integrated into the LED IR light source.

11. A method for determining a content of ethanol and of other monovalent alcohol in liquids, liquid samples containing at least water, ethanol or another alcohol, beverages, drugs, cosmetics, and for determining at least one additional content of extracts, sugars and fruit acid in the liquids, which comprises the steps of:
   performing one of providing a liquid in an analysis cell and flowing the liquid through a throughflow cell;
   irradiating the liquid via at least one light source formed with an LED, the light source emitting infrared (IR) radiation with a wavelength in a range from 1000 to 1500 nm by the further step of:
      irradiating the liquid one of temporally successively and practically simultaneously with a first IR radiation with a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other and with at least a second IR radiation with a second wavelength $\lambda 2$, at which the absorption coefficient of the ethanol or the other monovalent alcohol, Epsalk$\lambda 2$, and the absorption coefficient of the water, Epsw$\lambda 2$, are different from each other;
   measuring IR light absorption at least two different wavelengths of the infrared radiation resulting in measurement values;
   converting the measurement values to data reflecting at least an alcohol content of the liquid;
   forwarding in each case at least two real absorption values, which are determined currently by use of at least one IR detector, to a calculating and display unit for one of calculating and displaying and printing out of at least the alcohol content of the liquid; and
   measuring at least one of a density and an electrical conductivity of the liquid, and included in the evaluation together with results of corresponding comparison or calibration measurements.

12. A method for determining a content of ethanol and of other monovalent alcohol in liquids, liquid samples containing at least water, ethanol or another alcohol, beverages, drugs, cosmetics, and for determining at least one additional content of extracts, sugars and fruit acid in the liquids, which comprises the steps of:
   performing one of providing a liquid in an analysis cell and flowing the liquid through a throughflow cell;
   irradiating the liquid via at least one light source formed with an LED, the light source emitting infrared (IR) radiation with a wavelength in a range from 1000 to 1500 nm by the further step of:
      irradiating the liquid one of temporally successively and practically simultaneously with a first IR radiation with a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other and with at least a second IR radiation with a second wavelength $\lambda 2$, at which the absorption coefficient of the ethanol or the other monovalent alcohol, Epsalk$\lambda 2$, and the absorption coefficient of the water, Epsw$\lambda 2$, are different from each other;
   measuring IR light absorption at least two different wavelengths of the infrared radiation resulting in measurement values;
   converting the measurement values to data reflecting at least an alcohol content of the liquid;
   forwarding in each case at least two real absorption values, which are determined currently by use of at least one IR detector, to a calculating and display unit for one of calculating and displaying and printing out of at least the alcohol content of the liquid;
   for determining an alcohol concentration Calk in the liquid, evaluating actual IR light absorption values A$\lambda 1$, A$\lambda 2$, A$\lambda 3$ which were obtained for the different wavelengths as well as additionally values of at least one of density and conductivity of the liquid by a linear approximation method chosen from the group consisting of linear regression, multilinear regression and multiple regression, using appropriate reference values determined in previous calibration measurements.

13. A method for determining a content of ethanol and of another monovalent alcohol in liquids, the method includes the steps of:
   obtaining a liquid including at least water, ethanol or another alcohol, and at least one additional substance selected from the group consisting of sugars and fruit acids;
   performing one of providing the liquid in an analysis cell and flowing the liquid through a through flow cell;
   irradiating the liquid via at least one light source formed with an LED, the light source emitting infrared radiation with a wavelength in the range from 1000 to 1500 nm by the further step of:
      irradiating the liquid one of temporally successively and practically simultaneously with a first IR radiation having a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other, and with a second IR radiation having a second wavelength $\lambda 2$, where the absorption coefficient of the ethanol or the other monvalent alcohol, Epsalk$\lambda 2$, is greater than the absorption coefficient of the water, Epsw$\lambda 2$;
   measuring IR light absorption at least two different wavelengths of the infrared radiation resulting in measurement values;
   converting the measurement values to data of at least an alcohol content of the liquid;
   determining, via at least one IR detector, in each case at least two real absorption values;
   sending the two real absorption values to a calculating and display unit for a calculation and one of displaying and printing out of at least the alcohol content of the liquid;
   irradiating the liquid to be examined with a third IR radiation with a third wavelength $\lambda 3$, at which the absorption coefficient of the ethanol or the other monovalent alcohol, Epsalk$\lambda 3$, is clearly different from the absorption coefficient of the water, Epsw$\lambda 3$;
   performing the step of irradiating the liquid to be examined with the third IR radiation for increasing an accuracy of a result with regard to at least one of a content of the ethanol or the other monovalent alcohol and for at least one of compensation of turbidities in the liquid and for a determination of a content in the liquid of other components than ethanol or the other monovalent alcohol, the other components being selected from the group consisting of sugar, extracts, dyes, fruit acids and dyes;
   using the infrared radiation from an IR radiation source which optionally emits simultaneously two or three different wavelengths $\lambda 1$, $\lambda 2$ and $\lambda 3$; and
   using broad-band IR radiation from an IR radiation source from a LED-IR light source, whose peaks present a width at half value in a range from 50 to 100 nm.

14. The method according to claim 13,
wherein a peak maxima:
   of $\lambda 1$ is at 1160-1220 nm,
   of $\lambda 2$ is at 1270-1320 nm, and
   of $\lambda 3$ is at 1420-1470 nm.

15. The method according to claim 13, which further comprises:
   irradiating the liquid to be examined with the first IR radiation with the first wavelength $\lambda 1$, at which the absorption coefficient of the ethanol and the other monovalent alcohol, Epsalk$\lambda 1$, and of the water, Epsw$\lambda 1$, which are substantially identical to each other or at a maximum of a peak in the two wavelength-absorption coefficient diagrams or functions of the ethanol, the other monovalent alcohol and water; and
   irradiating the liquid to be examined with at least one of the second IR radiation and a third IR radiation with a wavelength $\lambda 2$ and $\lambda 3$, respectively, at which the absorption coefficients of the ethanol or the other monovalent alcohol, Epsalk$\lambda 2$ and Epsalk$\lambda 3$, and of the water, Epsw$\lambda 2$ and Epsw$\lambda 3$, are as different as possible from each other, and in each case are located in a plus/minus vicinity of a maximum or at a maximum of a peak in two wavelength-absorption coefficient diagrams or functions of the ethanol, the other monovalent alcohol and water.

16. The method according to claim 15, which further comprises using the IR radiation from an IR radiation source which optionally emits simultaneously two or three different wavelengths $\lambda 1$, $\lambda 2$ and $\lambda 3$, where a peak maxima:
   of $\lambda 1$ is at 1170-1190 nm;
   of $\lambda 2$ is at 1290-1300 nm; and
   of $\lambda 3$ is at 1425-1435 nm.

17. The method according to claim 15, which further comprises using the IR radiation from an IR radiation source which optionally emits simultaneously two or three different wavelengths $\lambda 1$, $\lambda 2$ and $\lambda 3$, where a peak maxima:
   of $\lambda 1$ is at approximately 1180 nm;
   of $\lambda 2$ is at approximately 1295 nm; and
   of $\lambda 3$ is at approximately 1430 nm.

18. The method according to claim 13, which further comprises during the measuring step, keeping constant a temperature of a sample located in the analysis cell or flowing through the through flow cell, so that a determination of the IR light absorption of the liquid to be examined is carried out at constant temperature of the liquid and/or a currently measured temperature of the liquid to be examined is taken into consideration in an evaluation of the measurement results, or electronically compensated with software.

19. The method according to claim 13, which further comprises keeping constant a temperature of the light source being an IR light source at least during an irradiation of the liquid and a determination of the value from its real absorption.

20. A method for determining a content of ethanol and of another monovalent alcohol in liquids, liquid samples containing at least water and alcohol, beverages, drugs, cosmetics, and for determining at least one of additional content extracts, sugars and fruit acid in a liquid, the method includes the steps of:
   performing one of providing the liquid in an analysis cell and flowing the liquid through a through flow cell;
   irradiating the liquid via at least one light source formed with an LED, the light source emitting infrared radiation with a wavelength in the range from 1000 to 1500 nm by the further step of:
      irradiating the liquid one of temporally successively and practically simultaneously with a first IR radiation having a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other, and with a second IR radiation having a second wavelength $\lambda 2$, where the absorption coefficient of the ethanol or the other monvalent alcohol, Epsalk$\lambda 2$, is greater than the absorption coefficient of the water, Epsw$\lambda 2$;

measuring IR light absorption at least two different wavelengths of the infrared radiation resulting in measurement values;

converting the measurement values to data of at least an alcohol content of the liquid;

determining, via at least one IR detector, in each case at least two real absorption values;

sending the two real absorption values to a calculating and display unit for a calculation and one of displaying and printing out of at least the alcohol content of the liquid; and using a photodetector to compensate or correct light intensity variations of the IR radiation;

wherein the photodetector is associated with a LED IR light source or integrated into the LED IR light source.

21. A method for determining a content of ethanol and of another monovalent alcohol in liquids, liquid samples containing at least water and alcohol, beverages, drugs, cosmetics, and for determining at least one of additional content extracts, sugars and fruit acid in a liquid, the method includes the steps of:

performing one of providing the liquid in an analysis cell and flowing the liquid through a through flow cell;

irradiating the liquid via at least one light source formed with an LED, the light source emitting infrared radiation with a wavelength in the range from 1000 to 1500 nm by the further step of:

irradiating the liquid one of temporally successively and practically simultaneously with a first IR radiation having a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other, and with a second IR radiation having a second wavelength $\lambda 2$, where the absorption coefficient of the ethanol or the other monvalent alcohol, Epsalk$\lambda 2$, is greater than the absorption coefficient of the water, Epsw$\lambda 2$;

measuring IR light absorption at least two different wavelengths of the infrared radiation resulting in measurement values;

converting the measurement values to data of at least an alcohol content of the liquid;

determining, via at least one IR detector, in each case at least two real absorption values;

sending the two real absorption values to a calculating and display unit for a calculation and one of displaying and printing out of at least the alcohol content of the liquid; and measuring at least one of a density and an electrical conductivity of the liquid, and included in the evaluation together with results of corresponding comparison or calibration measurements.

22. A method for determining a content of ethanol and of another monovalent alcohol in liquids, liquid samples containing at least water and alcohol, beverages, drugs, cosmetics, and for determining at least one of additional content extracts, sugars and fruit acid in a liquid, the method includes the steps of:

performing one of providing the liquid in an analysis cell and flowing the liquid through a through flow cell;

irradiating the liquid via at least one light source formed with an LED, the light source emitting infrared radiation with a wavelength in the range from 1000 to 1500 nm by the further step of:

irradiating the liquid one of temporally successively and practically simultaneously with a first IR radiation having a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other, and with a second IR radiation having a second wavelength $\lambda 2$, where the absorption coefficient of the ethanol or the other monvalent alcohol, Epsalk$\lambda 2$, is greater than the absorption coefficient of the water, Epsw$\lambda 2$;

measuring IR light absorption at least two different wavelengths of the infrared radiation resulting in measurement values;

converting the measurement values to data of at least an alcohol content of the liquid;

determining, via at least one IR detector, in each case at least two real absorption values;

sending the two real absorption values to a calculating and display unit for a calculation and one of displaying and printing out of at least the alcohol content of the liquid; and for determining an alcohol concentration Calk in the liquid, evaluating actual IR light absorption values A$\lambda 1$, A$\lambda 2$, A$\lambda 3$ which were obtained for the different wavelengths as well as additionally values of at least one of density and conductivity of the liquid by a linear approximation method chosen from the group consisting of linear regression, multilinear regression and multiple regression, using appropriate reference values determined in previous calibration measurements.

23. A method for determining a content of ethanol and of another monovalent alcohol in liquids, liquid samples containing at least water and alcohol, beverages, drugs, cosmetics, and for determining at least one of additional content extracts, sugars and fruit acid in a liquid, the method includes the steps of:

performing one of providing the liquid in an analysis cell and flowing the liquid through a through flow cell;

irradiating the liquid via at least one light source formed with an LED, the light source emitting infrared radiation with a wavelength in the range from 1000 to 1500 nm by the further step of:

irradiating the liquid one of temporally successively and practically simultaneously with a first IR radiation having a first wavelength $\lambda 1$, at which an absorption coefficient of the ethanol or the other monovalent alcohol, Epsalk$\lambda 1$, and an absorption coefficient of water, Epsw$\lambda 1$, are at least substantially identical to each other, and with a second IR radiation having a second wavelength $\lambda 2$, where the absorption coefficient of the ethanol or the other monvalent alcohol, Epsalk$\lambda 2$, is greater than the absorption coefficient of the water, Epsw$\lambda 2$;

measuring IR light absorption at least two different wavelengths of the infrared radiation resulting in measurement values;

converting the measurement values to data of at least an alcohol content of the liquid;

determining, via at least one IR detector, in each case at least two real absorption values;

sending the two real absorption values to a calculating and display unit for a calculation and one of displaying and printing out of at least the alcohol content of the liquid;

carrying out an IR absorption measurement with a device which contains the liquid to be examined and is disposed in the analysis cell or flows through the throughflow cell;

providing at least one of a temperature sensor for determining a current liquid temperature and a device for thermostatting the liquid for keeping a sample temperature constant;

providing two facing windows, which are permeable to IR radiation, and the light source being an infrared-LED radiation source behind a first of the windows, the infrared-LED radiation source emitting one of simultaneously and sequentially, the IR radiation with one of at least two different wavelengths $\lambda 1$, $\lambda 2$, and with three different wavelengths $\lambda 1$, $\lambda 2$, $\lambda 3$, and an IR radiation detector behind a second of the windows, the IR radiation detector being connected with a calculating unit for processing the absorption measurement values determined by the IR radiation detector, and a display unit for one of displaying and printing out at least the content of ethanol or of the monovalent alcohol in the liquid; and carrying out the IR absorption measurement with a device, where a photodetector or another radiation intensity measuring unit is associated with, or integrated in or on, the infrared LED radiation source for one of compensating and correcting variations in an intensity of the IR radiation emitted by the infrared LED radiation source, and connected with the calculating unit to allow data flow.

* * * * *